United States Patent [19]

Shih

[11] Patent Number: 4,748,238

[45] Date of Patent: * May 31, 1988

[54] CRYSTALLINE 1R,5S,6S,8R-1-METHYL-2-(N,N-DIMETHYL-CARBAMIMIDOYLMETHYLTHIO)-6-(1-HYDROXYETHYL)-1-CARBAPEN-2-EM-3-CARBOXYLIC ACID

[75] Inventor: David H. Shih, Manalapan, N.J.

[73] Assignee: Merck & Co., Inc., Rahway, N.J.

[*] Notice: The portion of the term of this patent subsequent to Dec. 15, 2004 has been disclaimed.

[21] Appl. No.: 873,262

[22] Filed: Jun. 6, 1986

Related U.S. Application Data

[63] Continuation of Ser. No. 589,369, Mar. 14, 1984, abandoned, which is a continuation of Ser. No. 365,066, Apr. 2, 1982, abandoned.

[51] Int. Cl.$^4$ .................... C07D 487/04; A61K 30/40

[52] U.S. Cl. ................................................. 540/350

[58] Field of Search ................. 540/310, 350; 514/210

[56] References Cited

U.S. PATENT DOCUMENTS

4,226,870  10/1980  Christensen et al. ........ 260/245.2 T
4,260,543   4/1981  Miller .......................... 260/245.2 T

FOREIGN PATENT DOCUMENTS

0071908  2/1983  European Pat. Off. .

Primary Examiner—Nicholas S. Rizzo
Attorney, Agent, or Firm—Raymond M. Speer; Hesna J. Pfeiffer

[57] ABSTRACT

Disclosed is crystalline 5R,6S,8R-1$\beta$-methyl-2-(N,N-dimethyl-carbaminidoylmethylthio)-6-(1-hydroxyethyl)-1-carbapen-2-em-3-carboxylic acid and a process for its preparation.

1 Claim, No Drawings

CRYSTALLINE 1R,5S,6S,8R-1-METHYL-2-(N,N-DIMETHYLCARBAMIMIDOYLMETHYLTHIO)-6-(1-HYDROXYETHYL)-1-CARBAPEN-2-EM-3-CARBOXYLIC ACID

This is a continuation of application Ser. No. 589,369 filed Mar. 14, 1984, now abandoned which is a continuation of Ser. No. 365,066 filed Apr. 2, 1982, now abandoned.

BACKGROUND OF THE INVENTION

This invention relates to crystalline 5R,6S,8R-1β-methyl-2-(N,N-dimethyl carbamimidoylmethylthio)-6-(1-hydroxyethyl)-1-carbapen-2-em-3-carboxylic acid and a process for its preparation.

The antibiotic 5R,6S,8R-1β-methyl-2-(N,N-dimethyl carbamimidoylmethylthio)-6-(1-hydroxyethyl)-1-carbapen-2-em-3-carboxylic acid (I) is disclosed in U.S. patent application Ser. No. 289,345 (filed Aug. 3, 1981), now abandoned, which is incorporated herein by reference to the extent that it discloses the preparation of amorphous I and its utility, whether amorphous or crystalline as an antibiotic:

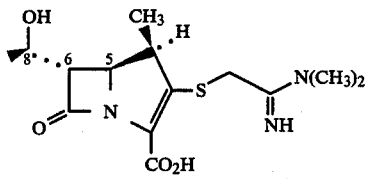

The crystalline form of I, which is disclosed and claim by this application is prepared from a lyophilized sample of I and is found to have unexpected stability in the solid state and unexpected, superior solubility in water.

DETAILED DESCRIPTION OF THE INVENTION

The described and claimed crystalline 5R,6S,8R-1β-methyl-2-(N,N-dimethylcarbamimidoylmethylthio)-6-(1-hydroxyethyl)-1-carbapen-2-em-3-carboxylic acid is unambiguously identified by the following parameters of the crystal which were obtained by X-ray powder diffraction.

The powder diffraction data are summarized in Table I. The tabulated results are the average of two runs for the same sample. The variations of the peak position (2Θ values) are within 0.1° (2Θ). The intensity ratios are within ten percent. Microscopically, under crossed polarized light, the crystalline compound I is birefringent and composed of well-formed, small, single crystals with rectangular or rod-like shapes.

TABLE I

X-Ray Powder Diffraction Data for crystal I

| Peak Position 2Θ (CuKα) | d-Spacing (Å) | Intensity I/I° | Peak Position 2Θ (CuKα) | d-Spacing (Å) | Intensity I/I° |
|---|---|---|---|---|---|
| 10.1 | 8.75 | 52 | 28.9 | 3.09 | 10 |
| 11.15 | 7.93 | 15 | 30.1 | 2.97 | 13 |
| 12.0 | 7.37 | 25 | 30.7 | 2.91 | 8 |
| 13.5 | 6.55 | 14 | 31.0 | 2.88 | 13 |
| 15.0 | 5.90 | 100 | 31.5 | 2.84 | 20 |
| 15.4 | 5.75 | 16 | 32.9 | 2.72 | 10 |
| 16.7 | 5.31 | 13 | 33.2 | 2.69 | 18 |
| 17.5 | 5.06 | 69 | 33.8 | 2.65 | 5 |
| 18.1 | 4.89 | 38 | 34.8 | 2.58 | 10 |
| 19.0 | 4.66 | 26 | 35.4 | 2.53 | 7 |
| 20.1 | 4.41 | 28 | 36.0 | 2.49 | 10 |
| 20.7 | 4.29 | 86 | 37.1 | 2.42 | 20 |
| 21.3 | 4.17 | 22 | 37.9 | 2.37 | 10 |
| 22.2 | 4.00 | 7 | 38.2 | 2.35 | 8 |
| 23.5 | 3.78 | 63 | 39.4 | 2.28 | 5 |
| 24.0 | 3.71 | 7 | 40.1 | 2.25 | 7 |
| 24.7 | 3.60 | 19 | 40.5 | 2.23 | 7 |
| 25.7 | 3.46 | 66 | 41.1 | 2.20 | 13 |
| 26.4 | 3.37 | 18 | 41.6 | 2.17 | 7 |
| 26.9 | 3.31 | 9 | 42.2 | 2.14 | 5 |
| 27.6 | 3.23 | 11 | 43.1 | 2.09 | 10 |
| 28.0 | 3.18 | 30 | | | |

Crystalline 5R,6S,8R-1β-methyl-2-(N,N-dimethyl carbamimidoylmethylthio)-6-(1-hydroxyethyl)-1-carbapen-2-em-3-carboxylic acid is prepared from a water/ethanol solution of 5R,6S,8R-1β-methyl-2-(N,N-dimethyl carbamimidoylmethylthio)-6-(-1-hydroxyethyl)-1-carbapen-2-em-3-carboxylic acid. The following specific example illustrates the crystallization.

EXAMPLE 1

Preparation of Crystalline 5R,6S,8R-1-β-Methyl-2-(N,N-dimethylcarbamimidoylmethylthio)-6-(1-hydroxyethyl)-1-carbapen-2-em-3-carboxylic acid The lyophilized solids of 5R,6S,8R-1-β-methyl-2-(N,N-dimethylcarbamimidoylmethylthio)-6-(1-hydroxyethyl)-1-carbapen-2-em-3-carboxylic acid (130 mg) were dissolved in 2.0 ml absolute methanol at room temperature. After stirring at room temperature for a few minutes, the white fine crystals started to form. The mixture was stirred for 30 minutes, then filtered to collect crystalline product (107 mg).

Fifty-six (56.0) mg of the crystals were further purified by re-crystallization from 1.0 ml water/methanol (1:9) solution at 0° C. to give slightly larger well-formed crystals with rectangular or rod-like shapes (50 mg). The crystalline product was characterized by X-ray powder diffraction (Table I). m.p. 200° C. (dec).

What is claimed is:

1. Crystalline 5R,6S,8R,1β-methyl-2-(N,N-dimethyl carbamimidoylmethylthio)-6-(1-hydroxyethyl)-1-carbapen-2-em-3-carboxylic acid, having the following X-ray powder diffraction parameters:

| Peak Position 2Θ (CuKα) | d-Spacing (Å) | Intensity I/I° | Peak Position 2Θ (CuKα) | d-Spacing (Å) | Intensity I/I° |
|---|---|---|---|---|---|
| 10.1 | 8.75 | 52 | 28.9 | 3.09 | 10 |
| 11.15 | 7.93 | 15 | 30.1 | 2.97 | 13 |
| 12.0 | 7.37 | 25 | 30.7 | 2.91 | 8 |
| 13.5 | 6.55 | 14 | 31.0 | 2.88 | 13 |
| 15.0 | 5.90 | 100 | 31.5 | 2.84 | 20 |
| 15.4 | 5.75 | 16 | 32.9 | 2.72 | 10 |
| 16.7 | 5.31 | 13 | 33.2 | 2.69 | 18 |
| 17.5 | 5.06 | 69 | 33.8 | 2.65 | 5 |
| 18.1 | 4.89 | 38 | 34.8 | 2.58 | 10 |
| 19.0 | 4.66 | 26 | 35.4 | 2.53 | 7 |
| 20.1 | 4.41 | 28 | 36.0 | 2.49 | 10 |
| 20.7 | 4.29 | 86 | 37.1 | 2.42 | 20 |
| 21.3 | 4.17 | 22 | 37.9 | 2.37 | 10 |
| 22.2 | 4.00 | 7 | 38.2 | 2.35 | 8 |
| 23.5 | 3.78 | 63 | 39.4 | 2.28 | 5 |
| 24.0 | 3.71 | 7 | 40.1 | 2.25 | 7 |
| 24.7 | 3.60 | 19 | 40.5 | 2.23 | 7 |
| 25.7 | 3.46 | 66 | 41.1 | 2.20 | 13 |
| 26.4 | 3.37 | 18 | 41.6 | 2.17 | 7 |
| 26.9 | 3.31 | 9 | 42.2 | 2.14 | 5 |
| 27.6 | 3.23 | 11 | 43.1 | 2.09 | 10 |
| 28.0 | 3.18 | 30 | | | |

* * * * *